United States Patent [19]

Gold et al.

[11] Patent Number: 5,037,404
[45] Date of Patent: Aug. 6, 1991

[54] CATHETER HAVING SECTIONS OF VARIABLE TORSION CHARACTERISTICS

[75] Inventors: Jeffrey G. Gold, Miami; Kevin F. Hahnen, Miramar; Mario J. Martinez, Miami, all of Fla.

[73] Assignee: Cordis Corporation, Miami Lakes, Fla.

[21] Appl. No.: 270,810

[22] Filed: Nov. 14, 1988

[51] Int. Cl.⁵ .................................... A61M 25/00
[52] U.S. Cl. ........................... 604/282; 87/11; 604/280
[58] Field of Search ........... 604/264, 280, 281, 282; 87/9, 11, 41, 44; 138/123, 124, 125, 130

[56] References Cited

U.S. PATENT DOCUMENTS

| | | | |
|---|---|---|---|
| 2,437,542 | 3/1948 | Krippendorf | 604/282 |
| 2,472,483 | 6/1949 | Krippendorf | 604/282 |
| 3,416,531 | 12/1968 | Edwards | 604/282 |
| 3,485,234 | 12/1969 | Stevens . | |
| 3,585,707 | 6/1971 | Stevens . | |
| 3,892,161 | 7/1975 | Sokol | 87/44 |
| 4,044,765 | 8/1977 | Kline | 604/282 |
| 4,516,972 | 5/1985 | Samson | 604/282 |
| 4,577,543 | 3/1986 | Wilson | 604/280 |
| 4,665,604 | 5/1987 | Dubowik | 604/282 |
| 4,706,670 | 11/1987 | Andersen et al. | 604/282 |
| 4,817,613 | 4/1989 | Jaraczewski et al. | 604/282 |
| 4,830,059 | 5/1989 | Silberstang | 138/130 |

FOREIGN PATENT DOCUMENTS

| | | | |
|---|---|---|---|
| 0726122 | 5/1932 | France | 604/280 |
| 1204216 | 1/1986 | U.S.S.R. | 604/280 |

Primary Examiner—Stephen C. Pellegrino
Assistant Examiner—Ralph A. Lewis
Attorney, Agent, or Firm—Gerstman & Ellis, Ltd.

[57] ABSTRACT

A flexible catheter comprises at least one resilient, flexible, tubular layer in telescoping relation with, and bonded to, a tubular wire sheath. A first catheter section includes the wire strands at a first angle to each other. A second catheter section includes the wire strands at a second angle to each other, with the second angle being different from the first angle so that the physical characteristics of the first and second catheter sections are different.

6 Claims, 1 Drawing Sheet

CATHETER HAVING SECTIONS OF VARIABLE TORSION CHARACTERISTICS

BACKGROUND OF THE INVENTION

In Stevens U.S. Pat. Nos. 3,485,234 and 3,585,707, tubular products such as catheters are disclosed which comprise an extruded plastic coating having a tubular, braided wire sheath disposed tightly about a plastic coating in telescoping relation therewith. A second, extruded layer of plastic is then applied over the braided sheath.

Such a catheter having a braided sheath increases the torsional stiffness of the catheter, so that torque may be better transmitted to typically the distal tip thereof with manipulation from the proximal catheter end. Such a characteristic is desirable to facilitate advancement, for example of an intravascular catheter through the branching blood vessel system of a patient. As the catheter is advanced, the surgeon may rotate the proximal end, and, by the invention of the Stevens patents, the distal end more accurately follows the desired rotational movement imparted to the catheter by the surgeon.

In some uses, it would be desirable for certain portions of the catheter to have more or less torsional rigidity than other portions of the catheter. For example, it might be desirable for the distal tip of the catheter to be very soft and pliable, with a low torsional rigidity, while an intermediate section of the catheter should have greater amounts of torsional rigidity to permit the transfer of torque to the tip area from the distal end.

On the other hand, it may be desirable for a catheter to have high torque at its tip but low longitudinal stiffness or "pushability". On the other hand, other sections such as the hub may desirably have high "pushability" or longitudinal rigidity, but with less torsional rigidity. Other sections of the catheter may desirably have intermediate properties in terms of torsional and longitudinal rigidity or stiffness.

By this invention, varying sections of the catheter may have varying torsional and longitudinal rigidity, in accordance with many different, desired, predetermined plans. This may be accomplished by variation of the relationships of the strands in the flexible, tubular, braided wire sheath provided to the catheter, to provide catheters with varying properties as may be desired.

DESCRIPTION OF THE INVENTION

This invention relates to a flexible catheter which comprises at least one resilient, flexible tubular layer in telescoping relation with and bonded to a tubular, wire sheath made of generally helically disposed, crossing wire strands.

In accordance with this invention, a first section of the catheter has such crossing wire strands which define a first angle to each other. A second section of the catheter has crossing wire strands of the sheath which define at least one second angle to each other. The second angle is different from the first angle, with the result that the physical characteristics of the first and second catheter sections are different. Particularly, in this circumstance the torsional and longitudinal rigidity of the respective catheter sections will vary.

Preferably, at least one second angle of crossing strands of a second section is at least 5 and preferably 10 to 40 degrees different from the first angle of the first section. If desired, a plurality of second sections may be present, the second sections defining strands having different second angles from each other. Alternatively, only a single second section with a single, second strand angle may be present.

It is generally preferred for the strands of a section to each define substantially similar angles to the catheter axis although if desired the angle of one of the set of helical strands in the sheath may define a substantially different angle to the catheter axis than the other set of helical strands in the same portion of the sheath.

Such tubular wire sheath of braided form is well known, having two sets of generally helically disposed strands which cross each other in engaging relation and weave in and out, over and under each other. Alternatively, the sets of crossing strands may be of purely helical configuration, with a first set and a second set of strands each defining a cylinder in their helical paths, with the second set of strands positioned inside the first set in telescoping relation therewith, without weaving or braiding of the crossing fibers. One set of strands defines a clockwise helix, and the other set a counterclockwise helix, so that the respective strands cross each other in straight manner, and bonded together.

Such tubular wire sheaths may be made on conventional and commercially available wire braiding machines or the like. The desired tubular, braided wire sheath may be made on a conventional wire braider, making use of a process controller of a design readily made by those skilled in the art to cause the "braid pitch" (the angle between the crossing braid strands) to be modified along the various sections of the braid that correspond to the first and second sections of the catheter. If desired, this may be accomplished by forming the braid on the flexible, tubular layer to bring them into bonded relation, or the braid may be applied by sliding it over the flexible, tubular layer.

The nonbraided crossing wire cylinders may have the strands of the two sets separately and sequentially wound on the flexible tubular layer, if desired, or such a sheath may be preformed. In any case, typically, an outer plastic or rubber layer is provided to enclose the tubular wire sheath and to facilitate the bonding of the sheath to the rest of the catheter.

In one preferred embodiment, the catheter of this invention may have a distal end and a proximal end, the strand angle of the tubular wire sheath of a first catheter section at the distal end being less than the corresponding strand angle of the wire sheath in a second catheter section which is spaced from the distal end by the first section. As a result of this, the first section can have lower torsional stiffness and greater longitudinal stiffness than the second section.

Additionally, it may be preferred for the strands of the tubular wire sheath adjacent the proximal end to be substantially parallel to the axis of the catheter. This provides a section with high "pushability" resulting from a high longitudinal stiffness, compared with the rest of the catheter. At the same time, the torsional stiffness may be low. This can facilitate the ease with which the physician can insert the catheter into a blood vessel or the like.

Typically, the catheter of the above specific type has strands of the braided wire sheath which all define substantially similar angles to the catheter axis in their respective sections.

The strands of "wire" used herein may be metallic, such as stainless steel, or nonmetallic, such as nylon, carbon fibers, KEVLAR fibers, or the like and may be of any desired cross-sectional shape. Also the strand cross section may change in shape or size along the length of the catheter in a manner independent of the strand angle.

Catheters in accordance with this invention may be manufactured by the technique as described in the previously cited Stevens patents. Additionally, any other conventional and desired method of manufacture may be used.

DESCRIPTION OF THE DRAWINGS

Referring to the drawings.

DESCRIPTION OF SPECIFIC EMBODIMENT

Figure 1:
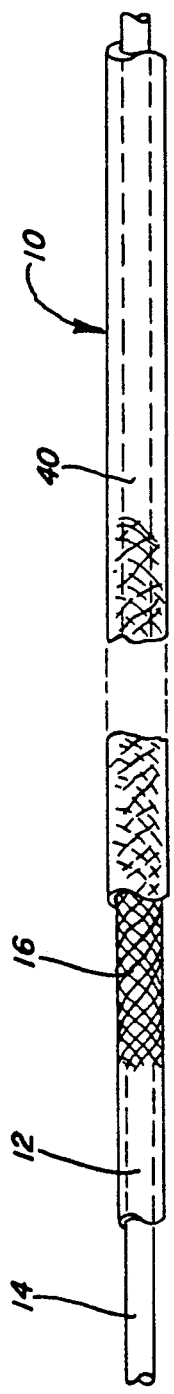
FIG. 1 is a fragmentary plan view of a catheter in accordance with this invention, with portions broken away, in process of manufacture.
Figure 2:
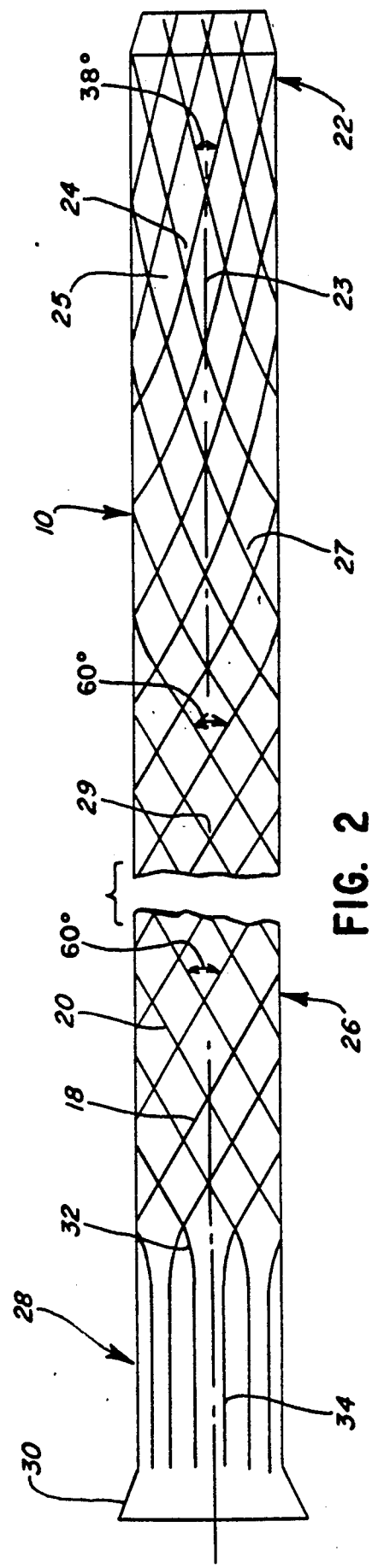
FIG. 2 is an enlarged plan view of the catheter of FIG. 1.

Referring to the drawings, a catheter 10 in accordance with this invention is shown. The specific catheter is made in accordance with the above cited Steven patents, with an inner plastic extrusion 12 being extruded on a mandrel 14 such as a silver wire. Inner plastic extrusion 12 may be of any appropriate material which is desirably used for a catheter such as polyethylene, nylon, PVC, polyurethane, or silicone rubber.

Either before or after curing inner extrusion 12 on mandrel 14, it may be placed into a conventional wire braiding machine to form a tubular, braided wire sheath 16 about the outer surface of inner extrusion 12. The braid may be laid down on inner extrusion 12 in the form of a set of counterrotating helical strands 18, 20, one of which set of strands rotates clockwise and the other counterclockwise. The braided strand arrangement may be conventional in configuration, except as otherwise taught herein.

Adjacent the distal end or catheter tip 22 the counterrotating sets of strands 18, 20 are formed to have a strand angle 24 to each other of, in this specific embodiment, 38 degrees, as indicated by reference numeral 24. Strand angle 24 is the angle that most closely faces in the direction of the catheter axis 23, rather than the side angle 25 which faces transversely thereto. It can also be seen that strands 18, 20 each have substantially identical angles to axis 23 in each section.

A transitional area 27 is provided on the catheter, in which the braider machine is set to change the strand angle from the strand angle of 38 degrees found in the tip section 22 to, in this specific embodiment, a strand angle 29 of 60 degrees in a second catheter section 26, as shown. Thus, second section 26 of the catheter has a lower longitudinal stiffness, and a higher torsional stiffness than tip section 22. Thus second section 26 permits the catheter to transmit torque well along its length, while tip section 22 is more yielding and resilient in terms of torque transmission.

Second catheter section 2 typically encompasses a great majority of the length of the catheter. However, at proximal end 28, a flared hub 30 may be formed typically during a later process step after the removal of mandrel 14. A second transitional area 32 of the catheter may be provided in which the wire braiding machine is set to change the strand angle from 60 degrees to parallel strand relation 34 in proximal end 28, as shown. The respective strand sections 34 are substantially parallel to catheter axis 23.

The effect of this is to increase the longitudinal rigidity of the catheter in end 28, while the torsional stiffness is minimized.

An outer plastic layer 40 may also be applied over tubular, braided wire sheath 16, as is conventional.

While the above embodiment in accordance with this invention is shown, it is contemplated that many other embodiments and angular relationships between the strands and respective catheter sections may be utilized, to provide catheters of many and varying characteristics as may be desired. For example, a central catheter section may be provided between sections 22 and 26, if desired, in which the strand angle is 45 degrees. A one inch transition section may be provided between the central section and tip section 22, and a three inch transition section may be provided between the central section and section 26.

Also, the wire sheath 16 may be made of "memory wire" such as Nitnol brand wire. Such wire can assume a predetermined shape upon heating to a certain temperature (or sometimes by electrical stimulation). Thus the cool, straight catheter can be designed to form a desired curve after implantation.

The above has been offered for illustrative purposes only, and is not intended to limit the scope of the invention of this application, which is as defined in the claims below.

That which is claimed is:

1. A flexible catheter which comprises:
a plastic tube that is resilient and flexible having a proximal end and a distal end, said plastic tube carrying a single wire sheath formed of generally helically disposed and braided crossing wire strands, said wire strands defining a first strand angle to each other along a first section of the tube toward the distal end of the tube and defining a second strand angle to each other along a second section of the tube between the first section and the proximal end of the tube, said strand angle being defined as the angle that generally faces in the direction of the tube axis, said first strand angle being less than said second strand angle by at least 5 degrees whereby the second section has higher torsional stiffness and less longitudinal stiffness than said first section, said tube carrying, between its proximal end and said second section, wire strands that are generally parallel to each other to increase the longitudinal rigidity of the catheter toward its proximal end while the torsional stiffness thereof is minimized.

2. A flexible catheter as defined by claim 1 wherein said wire sheath is formed of crossing metal wire strands.

3. A flexible catheter as defined by claim 1 in which the strand angle of the first section is substantially 38 degrees and the strand angle of the second section is substantially 60 degrees.

4. The flexible catheter as defined by claim 1 in which the strand angles of the first and second sections are substantially unchanging during use of said catheter.

5. The flexible catheter as defined by claim 1 in which said second strand angle is different from said first strands angle by at least 10 degrees.

6. The flexible catheter as defined by claim 1 in which said wire is stainless steel.

* * * * *